United States Patent
Botto et al.

(10) Patent No.: US 11,654,092 B2
(45) Date of Patent: May 23, 2023

(54) COSMETIC COMPOSITION CONTAINING BRANCHED ALKANES, SILICONES, AND NON-SILICONE FATTY COMPOUNDS

(71) Applicant: L'OREAL, Paris (FR)

(72) Inventors: Anna Botto, Cranford, NJ (US); Liliana Xavier, Mountainside, NJ (US)

(73) Assignee: L'OREAL, Paris (FR)

( * ) Notice: Subject to any disclaimer, the term of this patent is extended or adjusted under 35 U.S.C. 154(b) by 175 days.

(21) Appl. No.: 16/915,662

(22) Filed: Jun. 29, 2020

(65) Prior Publication Data

US 2021/0401695 A1 Dec. 30, 2021

(51) Int. Cl.
| | |
|---|---|
| *A61K 8/31* | (2006.01) |
| *A61K 8/892* | (2006.01) |
| *A61K 8/36* | (2006.01) |
| *A61Q 5/02* | (2006.01) |
| *A61Q 19/00* | (2006.01) |
| *A61Q 5/00* | (2006.01) |
| *A61K 8/92* | (2006.01) |

(52) U.S. Cl.
CPC ............ *A61K 8/31* (2013.01); *A61K 8/361* (2013.01); *A61K 8/892* (2013.01); *A61K 8/922* (2013.01); *A61Q 5/002* (2013.01); *A61Q 5/02* (2013.01); *A61Q 19/00* (2013.01)

(58) Field of Classification Search
CPC .......... A61K 8/31; A61K 8/361; A61K 8/892; A61K 8/922
See application file for complete search history.

(56) References Cited

U.S. PATENT DOCUMENTS 9,011,827 B2 * 4/2015 Bui .................... A61Q 1/04
424/64
2009/0123398 A1 5/2009 Laba et al.
2012/0003172 A1 1/2012 Desenne et al.

FOREIGN PATENT DOCUMENTS

| EP | 2548548 A1 | 1/2013 |
|---|---|---|
| JP | S63183517 A | 7/1988 |
| JP | 2009221143 A | 10/2009 |
| JP | 2015003886 A | 1/2015 |

OTHER PUBLICATIONS

French Search Report with Written Opinion, dated May 5, 2021 in French Patent Application No. 2008433, 9 pages.
Database GNPD Mintel XP055799330, Record ID 6821897, published Aug. 29, 2019, "Oil for Hair", 4 pages.

* cited by examiner

*Primary Examiner* — Snigdha Maewall
(74) *Attorney, Agent, or Firm* — The Marbury Law Group, PLLC

(57) ABSTRACT

The disclosure relates to cosmetic compositions for treating, caring for, and/or conditioning keratinous substrates, the compositions comprising branched alkanes, dimethiconols, silicones other than dimethiconols and having a viscosity at 25° C. of greater than or equal to $200 \times 10^{-6}$ m$^2$/s, and non-silicone fatty compounds other than the branched alkanes. The disclosure also relates to a cosmetic treatment process using this composition, and also the use of said composition for conditioning and/or caring for keratinous substrates.

22 Claims, No Drawings

COSMETIC COMPOSITION CONTAINING BRANCHED ALKANES, SILICONES, AND NON-SILICONE FATTY COMPOUNDS

FIELD OF THE DISCLOSURE

The present invention relates to a composition intended for the cosmetic treatment of human keratinous substrates such as the hair or skin, comprising branched alkanes, dimethiconol(s), silicones, and non-silicone fatty compounds other than the branched alkanes.

The invention also relates to a process for the cosmetic treatment of keratinous substrates, in which such a composition is applied to said substrates, and also to the use of this composition for conditioning and/or caring for keratinous substrates.

BACKGROUND

Consumers desire new and improved compositions for treating, caring for, and/or conditioning keratinous substances, such as skin or hair. Hair and skin are exposed to various intrinsic and extrinsic influences such as environmental factors, aging, and chemical factors. It is understood that different forms of haircare and skin care compositions can provide different benefits to address different problems of the skin or hair as a result these influences.

For example, the action of external atmospheric agents such as light and bad weather, and also by mechanical or chemical treatments, such as brushing, combing, dyeing, bleaching, permanent-waving and/or relaxing, or even repeated washing can damage and weaken hair fibers. Over time, hair may become dry, coarse, brittle or dull, especially in fragile areas, and more particularly at the ends.

Thus, to overcome these drawbacks, it is common practice to resort to haircare products using compositions intended to condition the hair, giving it satisfactory cosmetic properties, especially in terms of smoothness, sheen, softness, suppleness, lightness, a natural feel and good disentangling properties. For example, hair care compositions, such as hair conditioner and/or treatment compositions, may be used before or after the hair has been washed with shampoo and/or subjected to a chemical treatment in order to improve or return to the hair its natural luster, shine, and softness, or to improve the feel, appearance, and manageability of hair.

Haircare compositions, intended to be applied regularly to the hair, may be, for example, hair conditioners, masks or sera, and may be in the form of gels, hair lotions or care creams that are more or less thick. Skincare compositions may also be in the form of lotions, creams, and sera.

It is in particular known practice to use compositions in the form of oily sera, containing combinations of silicone oils or non-silicone oils.

However, silicone oils and non-silicone oils may have undesireable effects such as build-up on the hair and/or making the hair to feel heavy or weighed-down, and/or insufficient conditioning benefits such as smoothness, shaping, and/or moisture effect. Such compositions still too often result in excessive greasing of keratin fibers, which results in said fibers having a greasy or even tacky feel, and a lank, charged visual appearance.

Furthermore, compositions containing silicone oils, once applied to the hair, frequently result in effects that are not very pleasant to the touch; in particular the hair has a tendency to be coarse and/or to squeak (that is to say produce an unpleasant sound), especially when the strands of hair are rubbed together while sliding the fingers along the hair from the root to the end.

Additionally, the presence of silicones in a composition may present difficulties in preparing the compositions in various formulations.

Finally, the viscosity of these compositions is not always optimal, and does not make it possible to package them in a pump dispenser bottle.

SUMMARY OF THE DISCLOSURE

The present invention aims to provide compositions which do not have the drawbacks mentioned above, and which are capable of conditioning keratinous substrates such as hair and skin, in particular by giving them good cosmetic properties.

This aim is achieved by the present invention, a subject of which is in particular a cosmetic composition, which is preferably anhydrous, comprising:

(a) at least 30% by weight of one or more branched alkanes chosen from isohexadecane, isododecane, isodecane, isooctane, and mixtures thereof;

(b) from about 10 to about 25% by weight of one or more branched alkanes other than (a) and having from 7 to 70 carbon atoms;

wherein the weight ratio of (a) to (b) is >1;

(c) one or more dimethiconol(s);

(d) at least 10% by weight of one or more silicones, other than dimethiconols, having a viscosity at 25° C. greater than or equal to $200 \times 10^{-6}$ m$^2$/s;

(e) one or more non-silicone fatty compounds other than (a) or (b);

all weights being relative to the total weight of the composition.

The composition according to the invention makes it possible to condition and/or care for keratinous substrates such as hair and skin very satisfactorily. In particular, it makes it possible to significantly improve the sheen or shininess, the softness, the smoothness, the ease of disentangling of the hair, without weighing it down or making it greasy. The hair remains light, supple, and easy to style and to shape. The hair fibers are neither visually greasy nor greasy to the touch, and do not squeak when touched.

This composition also makes it possible to nourish and repair damaged hair, in particular at the ends, by sealing the ends, to control the frizziness of hair, and to facilitate the styling and straightening of curly or kinky hair.

Finally, the composition according to the invention has a suitable viscosity, allowing for the composition to be easily applied and distribute on a keratinous substrate and for making it possible to package it in a pump dispenser bottle. It is neither too fluid nor too viscous, and can be dispensed by a pump system.

The present invention is also related to a process for the cosmetic treatment of keratinous substrates such as skin or hair, in which the composition according to the invention is applied to the substrates.

Another subject of the present invention relates to the use of the composition as defined previously for the conditioning of keratinous substrates, in particular human keratin fibers such as the hair.

Other subjects, characteristics, aspects and advantages of the invention will emerge even more clearly on reading the description and the example that follows.

DETAILED DESCRIPTION OF THE DISCLOSURE

The present disclosure relates to a cosmetic composition, comprising:

(a) at least 30% by weight of one or more branched alkanes chosen from isohexadecane, isododecane, isodecane, isooctane, and mixtures thereof;

(b) from about 10 to about 25% by weight of one or more branched alkanes other than (a) and having from 7 to 70 carbon atoms;

wherein the weight ratio of (a) to (b) is >1;

(c) one or more dimethiconol(s);

(d) at least 10% by weight of one or more silicones, other than dimethiconols, having a viscosity at 25° C. greater than or equal to $200 \times 10^{-6}$ m$^2$/s;

(e) one or more non-silicone fatty compounds other than (a) or (b);

all weights being relative to the total weight of the composition.

The present disclosure also relates to a process of treating keratinous substrates, in particular hair, with the cosmetic compositions of the present invention, the process comprising applying said compositions onto the substrates.

In an embodiment, the process includes a step of rinsing or washing the keratinous substrate after treating the substrate with said cosmetic composition.

In an embodiment, the cosmetic composition of the invention is allowed to remain on the keratinous substrate for a period of time after treating the substrate with the composition.

The present disclosure also relates to a process of conditioning keratinous substrates such as skin or hair, the process comprising applying the cosmetic compositions of the present invention onto the substrates.

In an embodiment, the one or more branched alkanes (a) is present in an amount ranging from about 30 to less than 80% by weight, preferably from about 30 to about 75% by weight, more preferably from about 35 to about 70% by weight, and even more preferably from about 35 to about 65% by weight, relative to the total weight of the composition.

In an embodiment, the one or more branched alkanes other than (a) are chosen from branched alkanes having from 8 to 50 carbon atoms, or from 9 to 40 carbon atoms, or from 9 to 35 carbon atoms, or from 10 to 24 carbon atoms, or from 10 to 20 carbon atoms, and even more preferably, from 11 to 16 carbon atoms.

In an embodiment, the one or more branched alkanes other than (a) are chosen from C11, C12, C13, C14, C15, and C16 branched alkanes, alone or mixtures thereof.

In an embodiment, the one or more branched alkanes other than (a) are present in an amount ranging from about 12 to less than 25% by weight, preferably from about 14 to about 22% by weight, and more preferably from about 15 to about 20% by weight, relative to the total weight of the composition.

In an embodiment, the one or more branched alkanes (a) and the one or more branched alkanes other than (a) are present in a weight ratio of (a) to (b) ranging from about 4:1 to about 1.5:1, or from about 3.5:1 to about 2:1, or from about 3:1 to about 2.2:1, is preferably at about 2.5:1

In an embodiment, the one or more dimethiconol(s) are present in an amount ranging from about 0.5 to about 15% by weight, preferably, from about 1 to about 12% by weight, more preferably, from about 2 to about 10% by weight, relative to the total weight of the composition.

In an embodiment, the viscosity of the one or more silicones, other than dimethiconol(s), ranges from about $200 \times 10^{-6}$ m$^2$/s to about $2000 \times 10^{-6}$ m$^2$/s, or from about $250 \times 10^{-6}$ m$^2$/s to about $1500 \times 10^{-6}$ m$^2$/s, or from about $275 \times 10^{-6}$ m$^2$/s to about $1000 \times 10^{-6}$ m$^2$/s, or from about $300 \times 10^{-6}$ m$^2$/s to about $750 \times 10^{-6}$ m$^2$/s, or from about $325 \times 10^{-6}$ m$^2$/s to about $500 \times 10^{-6}$ m$^2$/s or from about $350 \times 10^{-6}$ m$^2$/s to about $450 \times 10^{-6}$ m$^2$/s $80 \times 10^{-6}$ m$^2$/s.

In an embodiment, the one or more silicones, other than dimethiconol(s) are chosen from polydialkylsiloxanes, preferably from polydimethylsiloxanes comprising trimethylsilyl end groups.

In an embodiment, the one or more silicones, other than dimethiconol(s) are present in an amount ranging from about 10 to about 50% by weight, preferably from about 12 to about 45% by weight and more preferably from about 15 to about 30% by weight relative to the total weight of the composition.

In an embodiment, the composition is free of decamethylcyclopentasiloxane, and preferably, is free of cyclopentasiloxane(s), and more preferably, is free of cyclomethicone.

In an embodiment, the composition is free of silicones having viscosities ranging from about 0.1 m$^2$/s to about 1 m$^2$/s.

In an embodiment, the one or more non-silicone fatty compounds other than (a) or (b) are chosen from triglycerides, esters, plant oils, and mixtures thereof.

In an embodiment, the one or more non-silicone fatty compounds other than (a) or (b) are present in an amount ranging from about 1 to about 20% by weight, preferably, from about 2 to about 18% by weight, more preferably, from about 5 to about 15% by weight, relative to the total weight of the composition.

In an embodiment, the composition is essentially free of amino silicones, including amodimethicone, and/or essentially free of dicaprylyl ether, and/or essentially free of hydrogentated polyisobutene, and/or dimethicones with a viscosity of less than 200 cSt ($200 \times 10^{-6}$ m$^2$/s) or greater than 2000 cSt ($2000 \times 10^{-6}$ m$^2$/s) at 25° C.

In an embodiment, the composition is free of silicones chosen from aminosilicones.

In an embodiment, the composition is free of hydrogentated polyisobutene.

In an embodiment, the composition is free of dimethicones with a viscosity of less than 200 cSt ($200 \times 10^{-6}$ m$^2$/s) or greater than 2000 cSt ($2000 \times 10^{-6}$ m$^2$/s) at 25° C.

In an embodiment, the composition is substantially anhydrous.

In an embodiment, the process for the cosmetic treatment of human keratinous substrates such as the hair or skin, comprises applying to the keratinous substrates the above-described composition of the invention.

In an embodiment, the process imparts conditioning properties to the keratinous substrates.

In an embodiment, the present invention is directed to a substantially anhydrous cosmetic composition comprising:

(a) from about 35 to about 70% by weight of isododecane;

(b) from about 14 to about 22% by weight of one or more branched alkanes other than (a) are chosen from C11-13 isoparaffin, C13-15 isoparaffin (2,6,10-trimethyldodecane), C13-16 isoparaffin, and mixtures thereof;

wherein the weight ratio of (a) to (b) is from about 3.0:1 to about 2.2:1;

(c) from about 1 to about 12% by weight one or more dimethiconol(s);

(d) from about 12 to about 45% by weight of one or more silicones, other than dimethiconols, having a viscosity at 25° C. of from about $300 \times 10^{-6}$ m$^2$/s to about $450 \times 10^{-6}$ m$^2$/s, and chosen from polydimethylsiloxanes comprising trimethylsilyl end groups;

(e) from about 2 to about 18% by weight of one or more non-silicone fatty compounds other than (a) or (b), and chosen from triglycerides;

all weights being relative to the total weight of the composition.

In the present description, and unless otherwise indicated:
the expression "at least one" is equivalent to the expression "one or more" and can be replaced therewith;
the expression "between" is equivalent to the expression "ranging from" and can be replaced therewith, and implies that the limits, as well as sub-ranges, are included.

According to the present application, the term "keratin fibers" denotes human keratin fibres and more particularly the hair.

Throughout the text herein below, the term "silicone" denotes, in accordance with what is generally accepted, any organosilicon polymer or oligomer of linear or cyclic, branched or crosslinked structure, of variable molecular weight, obtained by polymerization and/or by polycondensation of suitably functionalized silanes, and formed essentially from a repetition of main units in which the silicon atoms are linked together via oxygen atoms (siloxane bond —Si—O—Si—), optionally substituted hydrocarbon-based groups being directly linked via a carbon atom to said silicon atoms. The hydrocarbon-based groups that are the most common are alkyl groups, notably C1-C10 alkyl groups and in particular methyl, fluoroalkyl groups, the alkyl part of which is C1-C10, and aryl groups such as in particular phenyl groups.

In a manner known per se, the viscosity of the silicones, which is the kinematic viscosity, is measured at 25° C. and at atmospheric pressure (1 atm, 1.013×105 Pa) according to standard ASTM 445 Appendix C.

The weight-average molecular weights of the silicones may be measured by gel permeation chromatography (GPC) at ambient temperature (25° C.), as polystyrene equivalent. The columns used are µ styragel columns. The eluent is THF and the flow rate is 1 ml/min. 200 µl of a 0.5% by weight solution of silicone in THF are injected. Detection is performed by refractometry and UV-Vis spectrophotometry.

The Branched Alkane(s)

For the purposes of the invention, the term "alkane" is intended to mean a branched compound formed solely from carbon and hydrogen atoms.

The branched alkanes (or isoparaffins) according to the invention may include those alkanes which correspond to the formula CnH2n+2 with n being an integer with a value of at least 7 up to 70.

The Branched Alkane(s) (a):

The composition according to the present invention contains one or more branched alkanes (a) chosen from isohexadecane, isododecane, isodecane, isooctane, and mixtures thereof.

Particularly preferably, the branched alkane(s) (a) according to the invention comprise(s) 12 carbon atoms. A particularly preferred compound is isododecane. Isododecane may be commercially available as a raw material in combination with other compound(s) such as the raw material known by the tradename DOWSIL PMX-1505 FLUID supplied by the company Dow Corning (Dow Chemical). Isododecane may also be commercially available under the tradename PERMETHYL 99 A from the company Permethyl or under the tradename CREASIL IDCG from the company Cosmochem.

The branched alkane(s) (a) are advantageously present in a total content of at least 30% by weight, relative to the total weight of the composition.

According to various embodiments, the branched alkane(s) (a) are present in an amount ranging from about 30 to less than 80% by weight, preferably from about 30 to about 75% by weight, more preferably from about 35 to about 70% by weight, and even more preferably from about 35 to about 65% by weight, relative to the total weight of the composition.

According to one particularly preferred embodiment, the composition according to the invention contains isododecane, in an amount ranging from about 30 to less than 80% by weight, preferably from about 35 to about 70% by weight, more preferably from about 40 to about 60% by weight, and even more preferably from about 40 to about 55% by weight, relative to the total weight of the composition.

The Branched Alkane(s) (b):

The composition according to the present invention contains one or more branched alkanes other than (a) and having from 7 to 70 carbon atoms.

In various embodiments, the one or more branched alkanes other than (a) are chosen from branched alkanes having from 8 to 50 carbon atoms, or from 9 to 40 carbon atoms, or from 9 to 35 carbon atoms, or from 10 to 24 carbon atoms, or from 10 to 20 carbon atoms, and even more preferably, from 11 to 16 carbon atoms.

In various embodiments, the one or more branched alkanes other than (a) are chosen from C7, C8, C9, C10, C11, C12, C13, C14, C15, C16, C17, C18, C19, C20, C24, C35, C40, C50, and C70 branched alkanes, alone or mixtures thereof.

In various embodiments, the one or more branched alkanes other than (a) in the compositions of the present invention are mixtures of branched alkanes such as C11-C13 (INCI name: C11-13 isoparaffin, commercially available from Exxonmobil Chemical under the tradename ISOPAR L), and C13-C16 (INCI name: C13-16 isoparaffin, commercially available from Shin Etsu under the tradename MK-88). A particularly preferred mixture is C13-C16, C13-16 isoparaffin.

According to various embodiments, the one or more branched alkanes other than (a) are present in an amount of ranging from about 12 to less than 25% by weight, preferably from about 14 to about 22% by weight, and more preferably from about 15 to about 20% by weight, relative to the total weight of the composition.

According to various embodiments, the one or more branched alkanes (a) and the one or more branched alkanes other than (a) are present in a weight ratio of (a) to (b) ranging from about 4:1 to about 1.5:1, or from about 3.5:1 to about 2:1, or from about 3:1 to about 2.2:1, is preferably at about 2.5:1.

The Dimethiconol(s) (c):

The name dimethiconol denotes, in a manner known per se, polydimethylsiloxanes comprising dimethylsilanol end groups.

Preferably, the dimethiconol(s) according to the invention has (have) a weight-average molecular weight (Mw) of greater than 1000 daltons, preferably greater than 10 000 daltons, more preferably greater than 50 000 daltons, even more preferably, greater than 100 000 daltons.

By way of known compounds, mention may in particular be made of the compounds having the INCI name dimethiconol, commercially available from the company Dow Corning (Dow Chemical) under the trade names DOW CORNING 1515 Gum, DOWSIL 1515 Gum, and DOWSIL PMX-1505 FLUID.

The dimethiconol(s) are typically present in the compositions of the present invention in a total amount ranging from about 0.5 to about 15% by weight, preferably, from about 1 to about 12% by weight, more preferably, from about 2 to about 10% by weight, relative to the total weight of the composition.

The Silicone(s) (d):

The composition according to the invention contains one or more silicones having a viscosity at 25° C. of greater than or equal to $200 \times 10^{-6}$ m$^2$/s, i.e., 200 cSt ($1 \times 10^{-6}$ m$^2$/s=1 cSt).

Preferably, the viscosity of the silicone(s) (d) ranges from about $200 \times 10^{-6}$ m$^2$/s to about $2000 \times 10^{-6}$ m$^2$/s, or from about $250 \times 10^{-6}$ m$^2$/s to about $1500 \times 10^{-6}$ m$^2$/s, or from about $275 \times 10^{-6}$ m$^2$/s to about $1000 \times 10^{-6}$ m$^2$/s, or from about $300 \times 10^{-6}$ m$^2$/s to about $750 \times 10^{-6}$ m$^2$/s, or from about $325 \times 10^{-6}$ m$^2$/s to about $500 \times 10^{-6}$ m$^2$/s, or from about $350 \times 10^{-6}$ m$^2$/s to about $450 \times 10^{-6}$ m$^2$/s $80 \times 10^{-6}$ m$^2$/s.

Particularly preferred silicones (d) for use in the compositions of the present invention have a viscosity at 25° C. of from about $325 \times 10^{-6}$ m$^2$/s to about $500 \times 10^{-6}$ m$^2$/s, and preferably, from about $350 \times 10^{-6}$ m$^2$/s to about $450 \times 10^{-6}$ m$^2$/s $80 \times 10^{-6}$ m$^2$/s.

The silicone(s) c) are other than dimethiconols, that is to say that they are not polydimethylsiloxanes comprising dimethylsilanol end groups.

The silicone(s) c) are more particularly chosen from volatile and non-volatile silicones.

For the purposes of the present invention, the term "volatile silicone" is intended to mean a silicone that is capable of evaporating on contact with the skin or the hair in less than one hour, at ambient temperature and at atmospheric pressure. Such a silicone has in particular a saturation vapour pressure ranging from 0.13 to 40 000 Pa ($10^{-3}$ to 300 mmHg), in particular ranging from 1.3 to 13,000 Pa (0.01 to 100 mmHg), and more particularly ranging from 1.3 to 1300 Pa (0.01 to 10 mmHg).

For the purposes of the present invention, the term "non-volatile silicone" is intended to mean a silicone with a saturation vapour pressure of less than 0.13 Pa (0.01 mmHg).

The silicone(s) d) are more preferentially chosen from polydialkylsiloxanes, and in particular from polydimethylsiloxanes comprising trimethylsilyl end groups, also known under the names dimethicone and PDMS.

Mention may be made, among these polydialkylsiloxanes, in a non-limiting way, of the following commercial products under the tradenames DOWSIL SH 200 C FLUID 350 cSt, DOWSIL SH 200 C FLUID 350 CST, or XIAMETER PMX-200 SILICONE FLUID 350 CST from Dow Corning (Dow Chemical) or under the tradename MIRASIL DM 350 from Bluestar or BELSIL DM 350 from Wacker (Note: 350 cSt=$350 \times 10^{-6}$ m$^2$/s).

The silicone(s) (d) are typically present in an amount ranging from about 10 to about 50% by weight, preferably from about 12 to about 45% by weight and more preferably from about 15 to about 30% by weight relative to the total weight of the composition.

The Non-Silicone Fatty Compounds (e) [Other than (a) or (b)]

The non-silicone fatty compounds other than (a) or (b) that are present in the compositions of the present invention may be chosen from triglycerides, including synthetic and plant-based triglycerides, esters, plant oils, and mixtures thereof.

Suitable examples of triglycerides are caprylic/capric triglyceride (INCI name) and triglycerides having a chain length from and including C10 to C18. Thus, in some embodiments, triglycerides may comprise one or a blend of triglycerides having a chain length of C10, C11, C12, C13, C14, C15, C16, C17, and C18; one such example are triglycerides with the INCI name of C10-18 Triglycerides which is the triester of glycerin and a mixture of normal and branched chain C10-18 fatty acids.

Other suitable examples are dicaprylyl capric triglyceride, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

Additionally and/or alternatively, the triglycerides may be chosen from caprylic/capric/isostearic/adipic triglycerides, caprylic/capric/linoleic triglycerides, caprylic/capric/stearic triglycerides, glyceryltrilaurate/stearate, glyceryldi/tripalmitostearate, glyceryldi/tritristearate, caprylic triglyceride, caprylic/capric/lauric triglycerides, and mixtures thereof.

Suitable examples of esters or ester oils may be or include one or more diester oils. Non-limiting examples of diester oils include those chosen from diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisostearyl dimer dilinoleate, diisostearyl fumarate, and mixtures thereof.

Esters may also be or include one or more triester oils. Examples of triester oils that may, optionally be used, include triethyl hexanoin, trimethylolpropane triethylhexanoate, triisostearin, trimethylolpropane triisostearate, etc. Tetraester oils include pentaerythrityl tetraethylhexanoate, pentaerythrityl tetraisostearate, etc.

Esters may be or include one or more polyester oils. Non-limiting examples of polyester oils include polyglycerin fatty acid esters such as polyglyceryl-2 isostearate, polyglyceryl-2 diisostearate, polyglyceryl-2 triisostearate, polyglyceryl-2 tetraisostearate, etc.

The esters may also be high-viscosity ester oils such as those chosen from dipentaerythrityl hexa(hydroxystearate/stearate/rosinate), hydrogenated castor oil isostearate, hydrogenated castor oil dimer dilinoleate, (polyglyceryl-2 isostearate/dimer dilinoleate) copolymer, (phytosteryl/isostearyl/cetyl/stearyl/behenyl) dimer dilinoleate, bis(phytosteryl/behenyl/isostearyl) dimer dilinoleate, dimer dilinoleyl hydrogenated rosin condensation product, dimer dilinoleyl diisostearate, dimer dilinoleyl dimer dilinoleate, di(cholesteryl/behenyl/octyldodecyl) lauroyl glutamate, di(octyldodecyl/phytosteryl/behenyl) lauroyl glutamate, myristoyl methylalanine (phytosteryl/decyl tetradecyl), (diglycerin/dilinoleate/hydroxystearate) copolymer, etc Other suitable examples of esters include polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, and a mixture thereof. Specific examples of the esters of fatty acids, and/or esters of fatty alcohols are cetyl palmitate, cetyl stearate, myristyl myristate, myristyl stearate, cetyl myristate, and stearyl stearate (a mixture of which is referred to as "cetyl esters")). ethyl palmitate, isopropyl palmitate, ethyl myristate, isocetyl stearate, 2-ethylhexyl isononanoate, isononyl isononanoate, isodecyl neopentanoate and isostearyl neopentanoate.

Other suitable examples of esters include glyceryl esters.

Plant oils that can be used in the compositions of the present invention include sunflower oil, corn oil, soybean oil, marrow oil, grapeseed oil, sesame seed oil, hazelnut oil, apricot oil, macadamia oil, castor oil, avocado oil, olive oil, rapeseed oil, coconut oil, wheatgerm oil, sweet almond oil, apricot oil, safflower oil, coconut oil, camellina oil, jojoba oil, shea butter oil, canola oil, cottonseed oil, palm oil, peanut oil, safflower oil, sesame oil, sunflower oil, linseed oil, palm kernel oil, mustard oil, pennycress oil, pistachio oil, poppy oil, pine oil, colza oil, cade oil, peach kernel oil, coffee bean oil, and mixtures thereof.

Preferably, the composition according to the invention is free of cyclomethicone, that is to say of cyclic polydimethylsiloxane, in particular of cyclomethicone comprising from 4 to 6 silicon atoms.

The expression "free of cyclomethicone" is intended to mean that the composition according to the invention does not comprise cyclomethicone, or that, when the composition according to the invention contains one or more cyclomethicone(s), the latter are present in a total content of less than or equal to 0.1% by weight, preferably less than 0.05% by weight, relative to the total weight of the composition, even better still the composition is totally free of cyclomethicone (0% by weight).

Preferably, the composition according to the invention is free of cyclopentasiloxane(s).

The expression "free of cyclopentasiloxane(s)" is intended to mean that the composition according to the invention does not comprise cyclopentasiloxane(s), or that, when the composition according to the invention contains one or more cyclopentasiloxane(s), the latter are present in a total content of less than or equal to 0.1% by weight, preferably less than 0.05% by weight, relative to the total weight of the composition, even better still the composition is totally free of cyclopentasiloxane (0% by weight).

According to one particularly preferred embodiment, the composition according to the invention is free of decamethylcyclopentasiloxane.

The expression "free of decamethylcyclopentasiloxane" is intended to mean that the composition according to the invention does not comprise decamethylcyclopentasiloxane, or that, when the composition according to the invention contains decamethylcyclopentasiloxane, this compound is present in a total content of less than or equal to 0.1% by weight, preferably less than 0.05% by weight, relative to the total weight of the composition, even better still the composition is totally free of decamethylcyclopentasiloxane (0% by weight).

The Composition:

According to one preferred embodiment, the composition according to the invention is anhydrous or substantially anhydrous, that is to say that it comprises a water content of less than or equal to 4% by weight, preferably less than or equal to 2% by weight, more preferentially less than or equal to 1% by weight, even more preferentially less than or equal to 0.5% by weight, relative to the total weight of the composition. Preferably, the composition according to the invention is totally free of water (0%).

The composition according to the invention is advantageously clear, which gives it a particularly attractive aesthetic appearance that is highly sought after by users.

The composition according to the invention may also contain additives such as, for example, fragrances, fatty compounds other than (e), vitamins, plant extracts described above.

These additives may be present in the composition according to the invention in an amount ranging from 0% to 5% by weight relative to the total weight of the composition.

The composition according to the invention may be essentially free of amino silicones, including amodimethicone, and/or essentially free of dicaprylyl ether, and/or essentially free of hydrogenated polyisobutene, and/or dimethicones with a viscosity of less than 200 cSt ($200\times10^{-6}$ $m^2/s$) or greater than 2000 cSt ($2000\times10^{-6}$ $m^2/s$) at 25° C. The term "substantially free" or "essentially free" as used herein, with respect to aminosilicones and/or dicaprylyl ether, and/or hydrogenated polyisobutene and/or dimethicones with a viscosity of less than 200 cSt ($200\times10^{-6}$ $m^2/s$) or greater than 2000 cSt ($2000\times10^{-6}$ $m^2/s$) at 25° C. means that there is less than about 5% by weight of these specific material added to a composition (i.e. not part of a raw material added to the composition), based on the total weight of the compositions. Nonetheless, the compositions may include less than about 4 wt. %, 3 wt. %, 2 wt. %, 1 wt. %, less than about 0.5 wt. %, less than about 0.1 wt. %, or none of the specified materials Those skilled in the art will take care to select these optional additives and the amounts thereof so that they do not harm the properties of the compositions of the present invention.

The composition according to the invention is advantageously packaged in a non-aerosol device, such as in particular a pump dispenser bottle.

The Cosmetic Treatment Process:

A subject of the present invention is also a process for the cosmetic treatment of human keratinous substrates such as the hair or the skin, comprising the application to said fibres of a composition as described above.

Thus, the cosmetic compositions are useful in treating hair, for example, methods for conditioning hair or for providing conditioning benefits to hair. Non-limiting examples of conditioning benefits include imparting shine, color vibrancy, smoothness, softness, and discipline to the hair. The compositions may also be used to improve frizz control (i.e., to reduce frizz), and provide end seal of split ends or reduce the development of split ends. The process of treatment typically includes applying a composition to the hair, allowing the composition to remain on the hair for a period of time, and rinsing the composition from the hair. For example, the composition may be allowed to remain on the hair for about 5 seconds to about 30 minutes.

According to one embodiment, hair is then rinsed with water, and optionally washed with a shampoo and then rinsed with water, before being dried or left to dry.

In this embodiment, the composition according to the invention is applied for a leave-on time that may range from 1 to 15 minutes and preferably from 2 to 10 minutes.

According to one preferred embodiment, the hair is not rinsed after application of the composition. The composition is left on the hair for a period of time such as for about 30 minutes or about 60 minutes or for at least 4 hours. After the treatment with the invention composition, the hair can also undergo heat and/or mechanical treatment for drying and/or shaping, for example straightening by means of a heated iron or a blow dryer, and optionally accompanied by a brush or comb.

In some cases, the compositions are applied to the hair shortly after the hair has been cleansed or shampooed, for example, while the hair is still wet or damp. After the hair-treatment composition has remained on the hair for a period of time, it is rinsed from the hair and the hair may optionally be further treated with, for example, a typical conditioning compositions (a conditioner) and/or styled. Alternatively, the composition may be applied to the hair before the hair is cleansed or shampooed. For example, the composition may be applied to the hair (wet or dry) and allowed to remain on the hair for a period of time and rinsed from the hair. After rinsing the composition from the hair, the hair is cleansed or shampooed and optionally treated with a typical conditioning composition (a conditioner).

In some instances, the compositions are particularly useful as an interim treatment, e.g., a treatment to the hair immediately after shampooing the hair but before conditioning the hair or immediately after chemically treating the hair but before cleansing or shampooing the hair. For example, after rinsing a chemical treatment composition from the hair, a composition according to the instant disclosure can be applied to the hair and allowed to remain on the hair for a period of time and rinsed from the hair. After rinsing the composition from the hair, the hair may be cleansed or shampooed, optionally treated with a conditioning composition (a conditioner), and styled. The composition is also particularly useful as an interim treatment between shampooing and conditioning. After a shampoo has been rinsed from the hair, for example, while the hair is still damp, the composition of the present disclosure may be applied to the hair and allowed to remain on the hair for a period of time. After optionally rinsing the composition from the hair, the hair is conditioned (i.e., a conditioner is applied to the hair). After rinsing the conditioner from the hair, the hair may be styled, as desired.

The Use:

The present invention also relates to the use of a composition as described above, for conditioning keratinous substrates such as skin or hair, in particular human keratin fibers.

The composition can be used on wet or dry hair, in rinse-off or leave-on mode, and preferably in leave-on mode (that is to say that the hair is not rinsed after application of the composition).

Kits

The compositions of the present invention may be included in a kit, for example, a kit comprising the cosmetic composition of the present disclosure, a shampoo, and optionally a conditioner. The cosmetic composition, the shampoo, and the optional conditioner are separately contained or separately packaged. Kits according to the disclosure also include kits comprising a cosmetic composition of the present disclosure and one or more chemical hair-treatment compositions. Non-limiting examples of chemical hair-treatment compositions include hair lightening compositions, hair coloring compositions, hair relaxing compositions, hair straightening compositions, and hair shaping compositions (e.g., compositions to permanently curly hair).

The examples that follow serve to illustrate the invention without, however, being limiting in nature.

EXAMPLES

In the examples that follow, all the amounts are given, unless otherwise indicated, as mass percentages of active material relative to the total weight of the composition.

Example 1 Formulations

The following compositions were prepared from the ingredients of which the contents are indicated in the table below.

TABLE 1

| COMPONENT | INCI INGREDIENT NAME | INVENTION, A WT. % |
|---|---|---|
| (a) | ISODODECANE | 44.6 |
| (b) | C13-16 ISOPARAFFIN (1) | 17.6 |
|  | Weight ratio of a:b | 2.5:1 |
| (c) | DIMETHICONOL (2) | 7.9 |
| (d) | DIMETHICONE WITH A VISCOSITY OF 350 cSt or 350 × 10$^{-6}$ m$^2$/s (3) | 16.7 |
| (e) | CAPRYLIC/CAPRIC TRIGLYCERIDE | 10.0 |
|  | HIGHLY POLYMERIZED METHYL POLYSILOXANE (DIMETHICONE WITH A VISCOSITY >2000cSt | 2.4 |
| MISC. | ONE OR MORE OF FRAGRANCE/VITAMINS/PLANT EXTRACTS, ETC. | =/<2.0 |
|  | VISCOSITY OF COMPOSITION | about 75-95 UD* |

(1) Commercially available under the tradename MK-88 from Shin Etsu
(2) Commercially available under the trade names DOW CORNING 1515 Gum, DOWSIL 1515 Gum, and DOWSIL PMX-1505 FLUID from Dow Corning (Dow Chemical)
(3) Commercially available under the tradenames DOWSIL SH 200 C FLUID 350 cSt, DOWSIL SH 200 C FLUID 350 CST, or XIAMETER PMX-200 SILICONE FLUID 350 CST from Dow Corning (Dow Chemical) or under the tradename MIRASIL DM 350 from Bluestar or BELSIL DM 350 from Wacker (Note: 350 cSt = 350 × 10$^{-6}$ m$^2$/s)
*The viscosity of the composition was measured using a Rheomat 180 viscometer at about 25° C./spindle 2, 200 RPM for 30 seconds. The viscosity is expressed in UD ("Units of deflection").

Process of making the invention composition is described below (all-in-one process which does not require heat):

The dimethiconol and C13-16 isoparaffin were added to a main kettle and then mixed on medium speed. Dimethicone, caprylic/capric triglycerides were added to the kettle and the resulting mixture was mixed on medium speed.

TABLE 2

| | COMPARATIVE FORMULAS | | |
|---|---|---|---|
| INCI INGREDIENT NAME | B WT. % | C WT. % | D WT. % |
| ISODODECANE | 44.6 | 44.6 | QS |
| C13-16 ISOPARAFFIN AND/OR C11-13 ISOPARAFFIN | 17.6 | 17.6 | 28.0 |
| DIMETHICONOL | 7.9 | 7.9 | 7.9 |
| DIMETHICONE WITH A VISCOSITY OF 350 cSt | 16.6 | 14.1 | — |
| DIMETHICONE WITH A VISCOSITY OF <200 cSt | — | — | <10.0 |
| CAPRYLIC/CAPRIC TRIGLYCERIDE | — | 5.0 | 10.0 |
| AMODIMETHICONE | 2.5 | — | 2.0-3.0 |
| DICAPRYLYL ETHER | — | 5.0 | — |
| HYDROGENATED POLYISOBUTENE | 10.0 | 5.0 | — |
| ONE OR MORE OF FRAGRANCE/VITAMINS/PLANT EXTRACTS, ETC. | =/<2.0 | =/<2.0 | =/<0.2 |
| VISCOSITY OF COMPOSITION | 50-95 UD* | 50-95 UD* | |

*The viscosity of the composition was measured using a Rheomat 180 viscometer at about 25° C./spindle 2, 200 RPM for 30 seconds. The viscosity is expressed in UD ("Units of deflection").

TABLE 3

COMPARATIVE PRODUCT, E
Main Ingredients:

Dimethicone (~11 wt. %), isohexadecane (~30 wt. %), phenyl trimethicone (~2 wt. %), C13-14 isoparaffin, esters, diol, plant oils, water (aqua), plant extracts and plant powder, fragrance, vitamins.

Example 2 Performance Testing on Hair

Example 2A

The inventive composition was tested on hair according to the following procedure:

The inventive composition as well as compositions B and C were screened on hair swatches. Comparative Product E was also screened on hair swatch as the external benchmark. Five people ranked the swatches blindly for increased smoothness, increased discipline, decreased coating, and lack of transfer. The inventive composition (A) was unanimously chosen as the top spot by the majority of the participants for the cosmetic attributes.

Upon conducting the hair swatch study, for the compositions were subjected to in vivo testing on the hair of heads of human volunteers. The formulas A, B, and C were then tested on at least 5 heads vs E. Stylists (experts) evaluated the hair and provided their feedback as per the assessment table below. Both the swatches and in vivo tests showed a favourable result for the inventive composition, A.

The swatches were treated according to the protocol as follows:

Protocol Part I:
hair was first rinsed with water for about 10 seconds and excess water was wrung off the hair; A
a conventional sulfate-based shampoo was applied onto the damp hair at about 0.4 ml per gram of hair and was evenly distributed throughout the fibers;
shampoo was lathered on hair for about 30 seconds and left on hair for about a minute;
shampoo was rinsed off the hair;
swatches were allowed to dry.

Protocol Part II: Leave-on Treatment
test product was applied onto the dry hair at about 0.5 gram per 2.7 gram of hair and was evenly distributed throughout the fibers;
swatches were allowed to fully dry before being evaluated.

When applied onto hair, the inventive composition imparted to hair cosmetic properties of lubricty, gloss, smoothing, frizz control, ultimate absorption, and moisture without weighing the hair down.

Example 2B

The inventive and comparative compositions above were tested on hair. The performance and cosmetic attributes imparted to hair by these compositions compared to those by a commercial product, E, are indicated in the table below

| Formulas | Assessments |
| --- | --- |
| A vs E | Invention Composition A provided acceptable distribution effect, detangling power, and easy blow-dry effect on the hair. In addition, this formula offered a smoother touch from roots to ends, with good end seals, and positive frizz control effect. This formula offered the most homogeneous results in all hair types |
| B vs E | Comparative Composition B exhibited poor distribution effect, difficult in blow-drying, oily coating, and heavy weigh-down effect |
| C vs E | Comparative Composition C poor distribution effect, difficult in blow-drying, oily coating, and heavy weigh-down effect |

Example 2C Comparative Testing on Hair Against Comparative Composition F

The composition A (Invention), D (Comparative), and F (Comparative) were subjected to in vivo testing on the hair of heads of human volunteers.

Comparative Composition F contained over 90 wt. % of cyclopentasiloxane, about 7 wt. % of dimethiconol, and miscellaneous ingredients such as plant oils, vitamins and fragrance.

Surprisingly, the lower levels of the C13-C16 isoparaffin (17.6%) in Inventive Formula A together with the use of a medium viscosity PDMS at much higher amounts (16.7%) provided more smoothing effect, more even touch from roots to ends, and less oiliness to hair compared to the cosmetic attributes observed for Comparative composition D and Comparative composition F.

The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

The compositions described throughout this disclosure may be a "leave-on" product. A "leave-on" (also called leave-in) product refers to a hair treatment composition that is applied to hair and is not subjected to immediate rinsing and/or washing for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

The term "hair care" is interchangeable with the term "hair treatment" for purposes of the instant disclosure.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. Cosmetic composition comprising:
   (a) one or more branched alkanes chosen from isohexadecane, isododecane, isodecane, isooctane, or mixtures thereof, wherein the total amount of isohexadecane, isododecane, isodecane, isooctane, or mixtures thereof is at least 30% by weight;
   (b) one or more branched alkanes other than (a) and having from 7 to 70 carbon atoms, wherein the total amount of branched alkanes other than (a) and having from 7 to 70 carbon atoms ranges from about 10% to about 25% by weight;
   wherein the weight ratio of (a) to (b) is >1;
   (c) one or more dimethiconol(s);
   (d) one or more silicones other than dimethiconol(s), wherein the silicones other than dimethiconol(s) have a viscosity at 25° C. greater than or equal to $200 \times 10^{-6}$ m$^2$/s, and wherein the total amount of silicones with a viscosity at 25° C. of greater than or equal to $200 \times 10^{-6}$ m$^2$/s, other than dimethiconol(s), is at least 10% by weight; and
   (e) one or more non-silicone fatty compounds other than (a) or (b);
   all weights being relative to the total weight of the composition.

2. Composition according to claim 1, wherein the one or more branched alkanes (a) comprise isododecane.

3. Composition according to claim 1, wherein the total amount of branched alkanes (a) ranges from about 30% to less than 80% by weight, relative to the total weight of the composition.

4. Composition according to claim 1, wherein (b), the one or more branched alkanes other than (a), are chosen from branched alkanes having from 8 to 50 carbon atoms.

5. Composition according to claim 1, wherein (b), the one or more branched alkanes other than (a), are chosen from C11 branched alkanes, C12 branched alkanes, C13 branched alkanes, C14 branched alkanes, C15 branched alkanes, C16 branched alkanes, or mixtures thereof.

6. Composition according to claim 1, wherein the total amount of (b), branched alkanes other than (a), ranges from about 12% to less than 25% by weight, relative to the total weight of the composition.

7. Composition according to claim 1, wherein the composition comprises a total amount of branched alkanes (a) and a total amount of (b) branched alkanes other than (a) in a weight ratio of (a) to (b) ranging from about 4:1 to about 1.5:1.

8. Composition according to claim 1, wherein the total amount of (c) dimethiconol(s) ranges from about 0.5% to about 15% by weight, relative to the total weight of the composition.

9. Composition according to claim 1, wherein the viscosity of (d) the one or more silicones other than dimethiconol(s) ranges from $200 \times 10^{-6}$ m$^2$/S to about $2000 \times 10^{-6}$ m$^2$/s at 25° C.

10. Composition according to claim 1, wherein (d) the one or more silicones other than dimethiconol(s) are chosen from polydialkylsiloxanes.

11. Composition according to claim 1, wherein the total amount of (d) silicones other than dimethiconol(s) ranges from 10% to about 50% by weight, by weight relative to the total weight of the composition.

12. Composition according to claim 1, wherein the composition is free of decamethylcyclopentasiloxane.

13. Composition according to claim 1, wherein the composition is free of silicones having viscosities ranging from about 0.1 $m^2/s$ to about 1 $m^2/s$ at 25° C.

14. Composition according to claim 1, wherein (e) the one or more non-silicone fatty compounds other than (a) or (b) are chosen from triglycerides, esters, plant oils, or mixtures thereof.

15. Composition according to claim 1, wherein the total amount of (e) non-silicone fatty compounds other than (a) or (b) ranges from about 1% to about 20% by weight, relative to the total weight of the composition.

16. Composition according to claim 1, wherein:
the total amount of branched alkanes (a) ranges from about 40% to 50% by weight,
the total amount of branched alkanes (b) ranges from about 12% to 22% by weight,
the total amount of silicones (d) other than dimethiconol(s) ranges from about 15% to 25% by weight, and
the total amount of non-silicone fatty compounds (e) ranges from about 5% to 21% by weight and comprises one or more triglycerides,
wherein all amounts are relative to the total weight of the composition, and
wherein the weight ratio of (a) to (b) ranges from about 3.5:1 to about 2:1.

17. Composition according to claim 1, wherein the composition is substantially anhydrous.

18. Composition according to claim 1, wherein the composition is essentially free of amino silicones, and/or essentially free of dicaprylyl ether, and/or essentially free of hydrogentated polyisobutene, and/or essentially free of dimethicones with a viscosity of less than 200×10$^{-6}$ $m^2/s$ and/or essentially free of dimethicones with a viscosity of greater than 2000×10$^{-6}$ $m^2/s$ at 25° C.

19. Process for the cosmetic treatment of human keratinous substrates, comprising applying to the keratinous substrates the composition of claim 1.

20. The process of claim 19, wherein the process imparts conditioning and/or caring properties to the keratinous substrates.

21. A substantially anhydrous cosmetic composition comprising:
(a) one or more branched alkanes chosen from isohexadecane, isododecane, isodecane, isooctane, or mixtures thereof, wherein the total amount of isohexadecane, isododecane, isodecane, isooctane, or mixtures thereof ranges from about 35% to about 70% by weight;
(b) one or more branched alkanes chosen from C11-13 isoparaffin, C13-15 isoparaffin, C13-16 isoparaffin, or mixtures thereof, wherein the total amount of C11-13 isoparaffin, C13-15 isoparaffin, C13-16 isoparaffin, or mixtures thereof ranges from about 14% to about 22% by weight;
(c) one or more dimethiconol(s) wherein the total amount of dimethiconol(s) ranges from about 1% to about 12% by weight;
(d) one or more silicones chosen from polydialkylsiloxanes having a viscosity at 25° C. ranging from about 300×10$^{-6}$ $m^2/s$ to about 750×10$^{-6}$ $m^2/s$, wherein the total amount of polydialkylsiloxanes having a viscosity at 25° C. ranging from about 300×10$^{-6}$ $m^2/s$ to about 750×10$^{-6}$ $m^2/s$ ranges from about 12% to about 45% by weight; and
(e) one or more non-silicone fatty compounds chosen from triglycerides, esters, plant oils, or mixtures thereof, wherein the total amount of triglycerides, esters, plant oils, or mixtures thereof ranges from about 2% to about 18% by weight;
wherein all amounts are relative to the total weight of the composition, and
wherein the weight ratio of (a) to (b) ranges from about 3.5:1 to about 2:1.

22. Composition according to claim 21, wherein the one or more branched alkanes (a) comprises isododecane, and the one or more branched alkanes (b) comprises C13-16 isoparaffin.

* * * * *